US009086401B2

(12) United States Patent
Blick et al.

(10) Patent No.: US 9,086,401 B2
(45) Date of Patent: Jul. 21, 2015

(54) RADIO-FREQUENCY ION CHANNEL ANTENNA

(71) Applicant: Wisconsin Alumni Research Foundation, Madison, WI (US)

(72) Inventors: Robert H. Blick, Madison, WI (US); Abhishek Bhat, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 335 days.

(21) Appl. No.: 13/786,880

(22) Filed: Mar. 6, 2013

(65) Prior Publication Data
US 2014/0253153 A1   Sep. 11, 2014

(51) Int. Cl.
| | |
|---|---|
| *G01R 23/00* | (2006.01) |
| *G01R 27/08* | (2006.01) |
| *G01N 33/487* | (2006.01) |
| *G01R 31/317* | (2006.01) |
| *G01R 19/00* | (2006.01) |

(52) U.S. Cl.
CPC .......... *G01N 33/48728* (2013.01); *G01R 23/00* (2013.01); *G01R 31/31708* (2013.01); *G01R 19/0061* (2013.01)

(58) Field of Classification Search
CPC .. G01R 19/0061; G01R 23/00; G01R 1/2822; G01R 1/31708; G01R 33/32; G01N 33/48728

USPC ................ 324/707, 691, 649, 600, 464, 468, 324/76.11, 76.12, 76.19, 76.21, 76.22, 324/76.39, 76.41, 310, 313
See application file for complete search history.

(56) References Cited

U.S. PATENT DOCUMENTS

| | | | | |
|---|---|---|---|---|
| 6,063,260 | A  * | 5/2000 | Olesen et al. | 205/793 |
| 6,117,291 | A  * | 9/2000 | Olesen et al. | 204/415 |
| 8,217,665 | B2 | 7/2012 | Blick et al. | |
| 2005/0009171 | A1 * | 1/2005 | Fertig et al. | 435/287.2 |

OTHER PUBLICATIONS

Radio frequency tank circuit for probing planar lipid bilayers, A Bhat, J Rodriguez, H Qin, H C Shin, H Shin, J Clobes, D Kreft, J Park, E Stave, M Yu and R H Blick.

* cited by examiner

*Primary Examiner* — Hoai-An D Nguyen
(74) *Attorney, Agent, or Firm* — Boyle Fredrickson, S.C.

(57) ABSTRACT

An antenna is used for radio frequency measurements of cell wall impedance changes due to ion channels. The antenna provides enhanced direct readout of lipid bilayers and cells containing pores and ion channels. The antenna is placed around a nanopore, which may be fabricated from glass, quartz or other material, and is shaped to provide an enhanced sensitivity to electrical activity in the vicinity of the nanopore. As such, the antenna may be of a class of bi-cone- or other stub-antennas providing high gain and broad bandwidth, for example a planar variant of a "bow-tie" antenna. Accordingly, improved sensitivity of at least an order of magnitude may be achieved over past systems.

20 Claims, 5 Drawing Sheets

RADIO-FREQUENCY ION CHANNEL ANTENNA

BACKGROUND OF THE INVENTION

The present invention relates to systems and methods for investigating ion transport through cellular membranes, and in particular to systems and methods that may provide rapid measurement of ion channel activity.

The lipid bilayers that make up cell membranes include ion channels that control the flow of ions into and out of cells. Certain ion channels open in response to signaling molecules including naturally occurring signaling molecules and drug molecules. In the development of therapeutic drugs it is necessary to determine the effect of the drug on ion channels either to avoid adverse effects or to create a positive therapeutic effect for the treatment of ion-channel related diseases.

Analysis of the response of ion channels may be conducted with a so-called "patch-clamp," traditionally a micropipette adhered to the surface of a cell by a slight suction. An electrical connection across the membrane of the cell is then made by one of a number of techniques, for example, by applying a sharp suction pulse to the pipette to open a hole in the cell wall. Measurement of small electrical changes across the cell membrane made by a miniature electrode inserted into or near the opening may then be used to deduce the flow of ions through the ion channels. The small amounts of electrical current involved in these measurements require an extremely high resistance seal between the pipette and the cell wall (a Giga-ohm seal).

Drug screening often requires making many ion-channel measurements. Accordingly the pipette having a single opening has been replaced with a plate having multiple small pores each of which may accept a cell. The plate array allows the parallel processing of multiple cells and may be more readily integrated into automated equipment.

The sensitivity of measurements of small current flows through ion channels can be significantly limited by the poor electrical characteristics of a bare electrode immersed in the aqueous medium inside or outside of the cell. As a result, rapid changes in ionic transport may be difficult to resolve. It is desirable to understand and resolve such changes, for example, in the context of medications that may affect the human body.

Improvements in such systems, including as described in U.S. Pat. No. 8,217,665, which is hereby incorporated by reference, provide a patch-clamp system employing high-frequency characterization of cell wall membranes. Changes in the frequency response of a tank circuit incorporating the cell wall membrane impedance provides highly sensitive and highly time-resolved measurements of ion channel activity. However, the above systems are typically limited by their data acquisition speeds and resolutions.

SUMMARY OF THE INVENTION

The present invention provides an antenna for radio frequency measurements of cell wall impedance changes due to operation of ion channels. An antenna and circuitry may be used to amplify a signal produced from a capacitance change at a single nanopore.

In accordance with the present invention, an antenna is used to provide enhanced direct readout of lipid bilayers and cells containing pores and ion channels. Pores in cells typically remain in an open state but may be blocked by small molecules. Ion channels in cells may open and close in dependence of an external trigger. The antenna is placed around a nanopore, which may be fabricated from glass, quartz or other material, and is shaped to provide an enhanced sensitivity to electrical activity in the vicinity of the nanopore. As such, the antenna may be of a class of bi-cone- or other stub-antennas providing high gain and broad bandwidth, for example, a planar variant of a "bow-tie" antenna. Improved sensitivity of at least an order of magnitude may be achieved over past systems. This may provide, for example, an improved technique with the ability to better resolve the fine interactions between medicines and changes in ion channel activity, which may have a tremendous impact for finding new medicines via high-throughput screening.

Specifically the present invention provides an analyzer for membranes with ion channels. An electrically insulating support may be adapted to provide a support region for holding a cellular membrane. An antenna may provide a first and second antenna lobe on opposite sides of the support region. The first and second antenna lobes may be have spaced apart apexes proximate to the support region with the lobes widening from the apexes with increased distance from the support region along an axis, and with the widening constrained substantially within bounding cones with one cone each sharing the apex of each lobe and having cone axes aligned with the axis. Circuitry may provide a radio frequency signal across the antenna lobes that determines changes of electrical flow across the cellular membrane when positioned in the support region.

The circuitry may comprise a radio signal amplifier and a measurement circuit.

It is thus a feature of at least one embodiment of the invention to employ standard hardware for generating and measuring values relating to the cell membrane.

The angle of each cone may be between 25 and 40 degrees.

It is thus a feature of at least one embodiment of the invention to provide a high sensitivity antenna suitable for ion channel measurement.

The antenna lobes may substantially form a bi-cone antenna.

It is thus a feature of at least one embodiment of the invention to employ characteristics of traditional bi-cone antenna for improved measurements.

The first and second antenna lobes may be comprised of a metallic micro-strip.

It is thus a feature of at least one embodiment of the invention to provide an antenna having controlled and well-defined electrical characteristic for optimal transmission and reception.

After the first and second antenna lobes widen the first and second antenna lobes may straighten through an increased distance along the same axis.

It is thus a feature of at least one embodiment of the invention to provide an antenna structure geometrically formed to have lengths on either side of the support region.

After the second antenna lobe straightens the second antenna lobe may widen in opposite directions to either side then may substantially form around either side of the first antenna lobe.

It is thus a feature of at least one embodiment of the invention to provide an antenna structure geometrically formed to present a half "bow-tie" shape.

The radio frequency signal may be in excess of 100 MHz and may be in the GHz and THz ranges.

It is thus a feature of at least one embodiment of the invention to permit measurement of extremely small changes in impedance values.

These particular features and advantages may apply to only some embodiments falling within the claims and thus do not define the scope of the invention.

DETAILED DESCRIPTION OF THE PREFERRED EMBODIMENT

Figure 1:
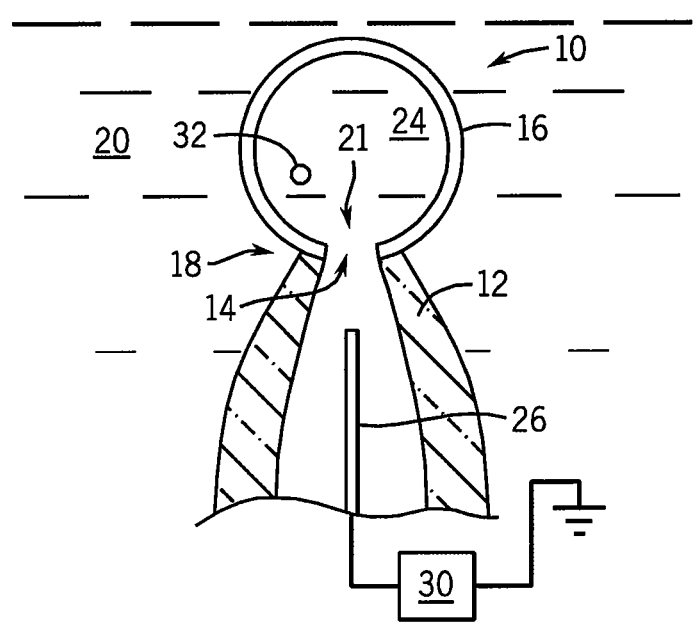
FIG. 1 is an elevational cross-section of a prior art patch-clamp used for whole-cell recording.

Referring now to FIG. 1, a prior art whole-cell patch-clamp 10 may employ a micropipette 12 having an aperture 14 to which a cell 16 is drawn by suction. The cell 16 may attach to the aperture 14 to create a Giga-ohm seal to a lip 18 of that aperture. The cell 16 may otherwise be suspended in a liquid medium 20 providing an environment desired for a particular experiment.

A sharp suction may be used to open a hole 21 in the cell wall of the cell 16 providing a low resistance path from the interior cytoplasm of the cell through a solution 24 to a microelectrode 26 within the micropipette 12. The microelectrode 26 is typically a silver electrode coated with silver chloride for electrochemical stability.

A sensitive current detector 30 may be connected between the microelectrode 26 and the liquid medium 20 to measure the passage of ions 32 through channels in the cell wall. The current detector 30 may provide for a voltage-clamping action, if desired, using a conventional voltage feedback circuit. Generally the bare microelectrode 26 provides electrical characteristics that severely limit the frequency of the measure of ionic currents. Further, only resistive impedance of the cell wall may be determined.

Figure 2:
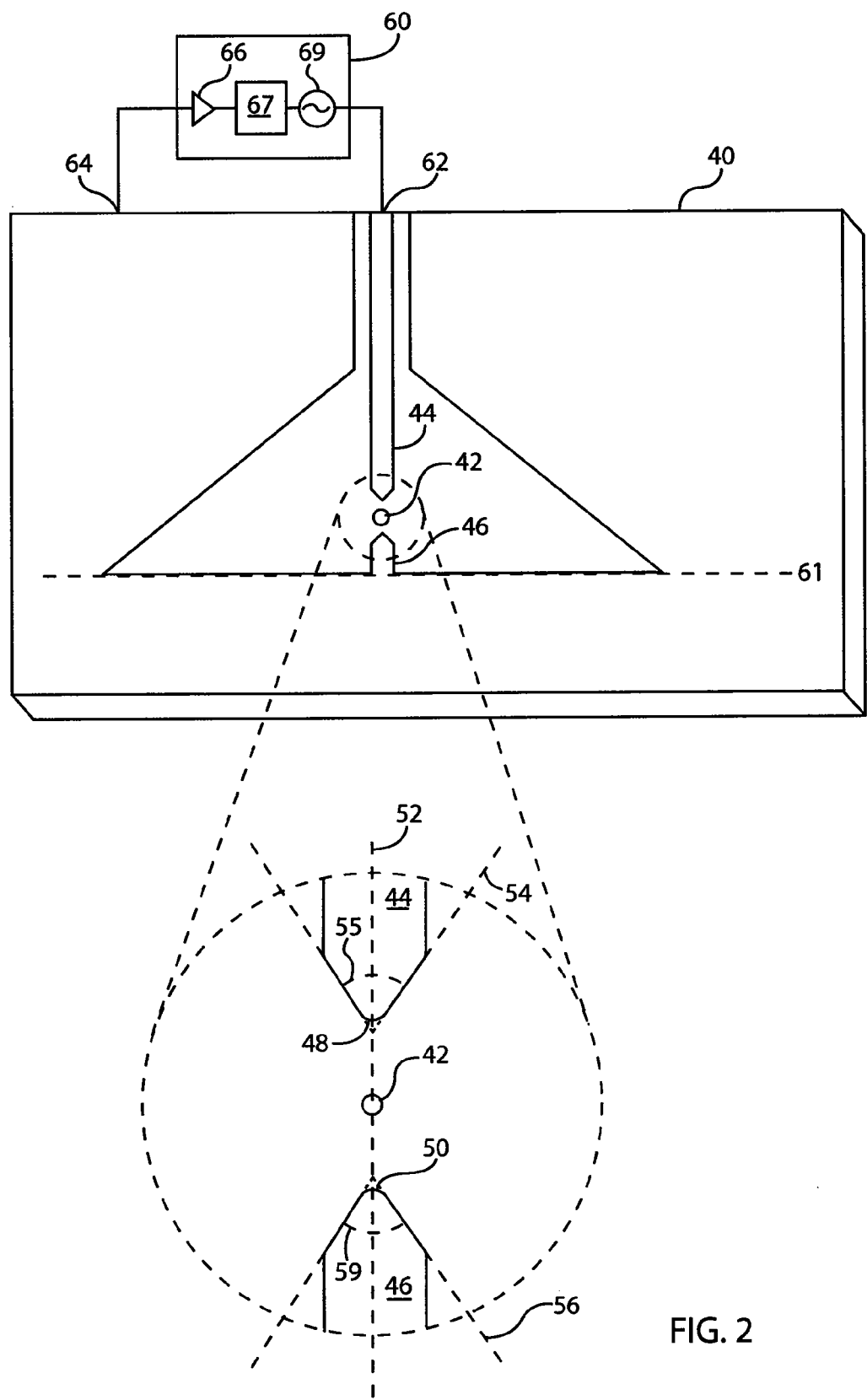
FIG. 2 is a diagram of a radio frequency cell membrane analyzer in accordance with an embodiment of the invention.

Referring now to FIG. 2, the present invention provides an electrically insulating support substrate 40 having a single nanopore aperture 42 for holding a cellular membrane fixed with respect to the substrate 40. The cellular membrane may be held using the whole cell technique described above, or by a variety of other techniques well known in the art. The single nanopore aperture 42 may be, for example, between 500 nm and 250 μm in diameter.

An antenna providing a first antenna lobe 44 and a second antenna lobe 46 is positioned on opposite sides of the single nanopore aperture 42 and cellular membrane. The antenna lobes 44 and 46 each have spaced apart apexes 48 and 50, respectively, proximate to the single nanopore aperture 42 support region. The antenna lobes 44 and 46 each widen from the apexes 48 and 50 with increased distance from the single nanopore aperture 42 along an axis 52. The widening is constrained substantially within bounding cones 54 and 56, respectively, with one cone sharing the apexes 48 and 50 of each of the antenna lobes 44 and 46 and having cone axes aligned with the axis 52. The angles 55 and 59 of each cone are between 25 and 40 degrees. The antenna lobes accordingly substantially form a bi-cone antenna.

After the antenna lobes 44 and 46 widen, the antenna lobes 44 and 46 straighten through an increased distance along the same axis 52. After the second antenna lobe 46 straightens, the second antenna lobe 46 widens in opposite directions to either side along the axis 61, then substantially forms around either side of the first antenna lobe 44. The second antenna lobe 46 may accordingly present a half "bow-tie" geometric shape around the first antenna lobe 44. The "bowtie" configuration approximates a bi-cone antenna in two dimensions and may be considered a class of bi-cone antennas. Alternative embodiments may provide other stub-antennas having high gain and broad bandwidth. In one example, a planar variant of a "bow-tie" antenna may be used.

Antenna circuitry 60 provides a radio frequency signal via radio signal generator 65 to the first antenna lobe 44 via terminal 62. In turn, a signal produced from a capacitance change at the single nanopore 42 is received by the second antenna lobe 46. The signal is then sensed by antenna circuitry 60 via terminal 64. The antenna circuitry 60, in turn, amplifies the signal via radio signal amplifier 66 and determines changes of impedance across the cellular membrane from measurement of the change in electrical resonance via measurement circuit 67. Terminals 62 and 64 may be implemented via standard high-frequency coaxial connectors. Measurement circuit 67 also provides a measureable output indicating the determined change in impedance.

Figure 3:
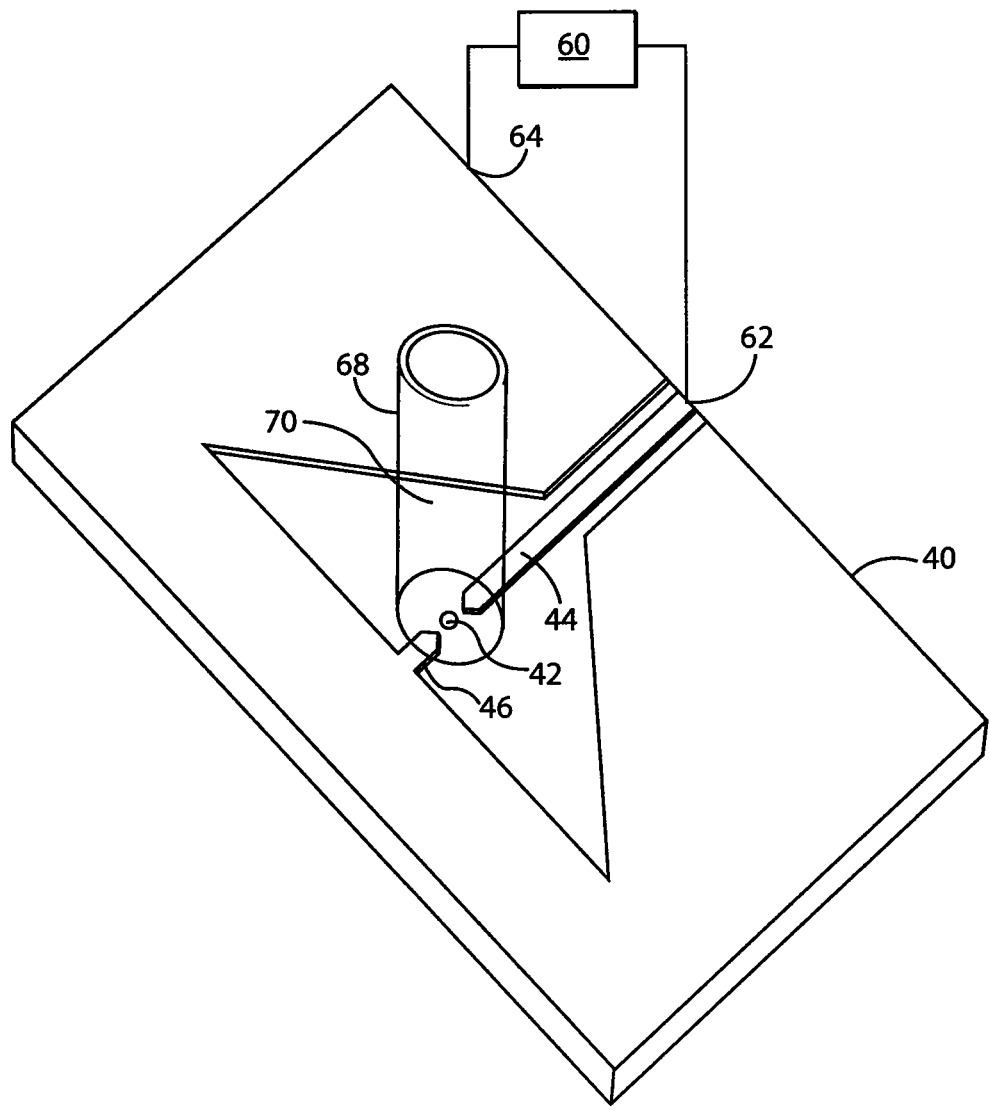
FIG. 3 is an isometric view of a radio frequency cell membrane analyzer in accordance with an embodiment of the invention.

Referring now to FIG. 3, an isometric view of a radio frequency cell membrane analyzer in accordance with an embodiment of the invention. A fluid chamber cylinder 68 for holding a liquid medium 70, such as saline water, may be provided over the single nanopore aperture 42 for holding the cellular membrane. The antenna lobes 44 and 46, where they contact the liquid medium 70, are a conductive material. In one embodiment, for most of their lengths, the antenna lobes 44 and 46 may be insulated from the liquid medium 20 and, in this insulated portion, the antenna lobes 44 and 46 may be a metallic micro-strip having a controlled and well-defined electrical characteristic such as will provide optimal antenna transmission and reception. The fabrication of the micro-strips may be made by using well-known integrated circuit techniques or surface coating methods. Other materials, such as Aluminum, Copper, Silver, Silver Chloride, Gold, Titanium Gold, Zinc or related compounds, may alternatively be used. The thickness of the metallic micro-strip may also vary according to material used, which may in turn vary the approximate resonant frequency and amplitude as shown by way of example in Table 1.

TABLE 1

| Type of Material | Approximate Thickness | Approximate Resonant Frequency | Approximate Amplitude (dB) |
| --- | --- | --- | --- |
| Aluminum | 165 nm | 253 MHz | −49.31 |
| Copper | 115 nm | 262 MHz | −47.11 |
| Gold | 165 nm | 248 MHz | −51.43 |
| Silver | 105 nm | 260 MHz | −32.19 |
| Titanium Gold | 165 nm | 259 MHz | −54.00 |
| Zinc | 295 nm | 247 MHz | −19.87 |

Figure 4:
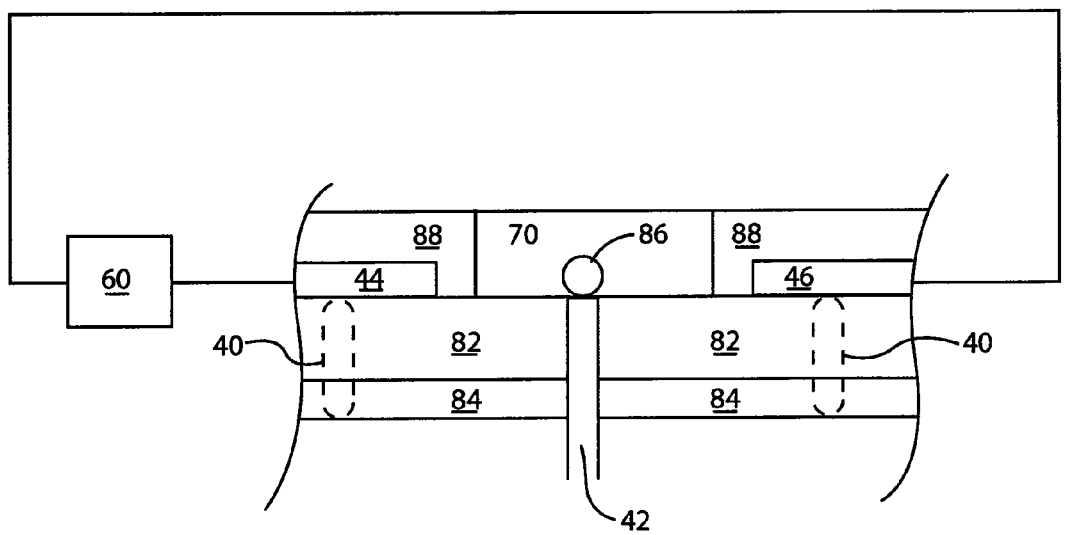
FIG. 4 is an elevated cross-section of a radio frequency cell membrane analyzer in accordance with an embodiment of the invention.

Referring now to FIG. 4, an elevated cross-section of the present invention provides the electrically insulating support substrate 40 which may comprise a first layer 82 of glass or quartz over an optional second layer 84 of thin Polydimethylsiloxane ("PDMS"), such as Sylgard 184 Silicone Elastomer from Dow Corning Corp. The single nanopore aperture 42 provides a drilled hole through the substrate 40 for holding cellular membrane 86 fixed with respect to the substrate 40. On either side of the single nanopore aperture 42 and above the first layer 82 are the antenna lobes 44 and 46 comprised of metallic micro-strip. Above of the antenna lobes 44 and 46 an optional third layer 88 of thin PDMS may be applied and above the single nanopore aperture 42 and cellular membrane 86 is the liquid medium 70. In an embodiment, the liquid medium 70 may be in contact with the second antenna lobe 46, up as shown in FIG. 2, to substantially near the second antenna lobe 46 forming around either side of the first antenna lobe 44. Antenna circuitry 60 provides a radio frequency signal and determines changes of impedance across cellular membrane 86 from a measurement of a change in electrical resonance as described above with respect to FIG. 2.

Figure 5:
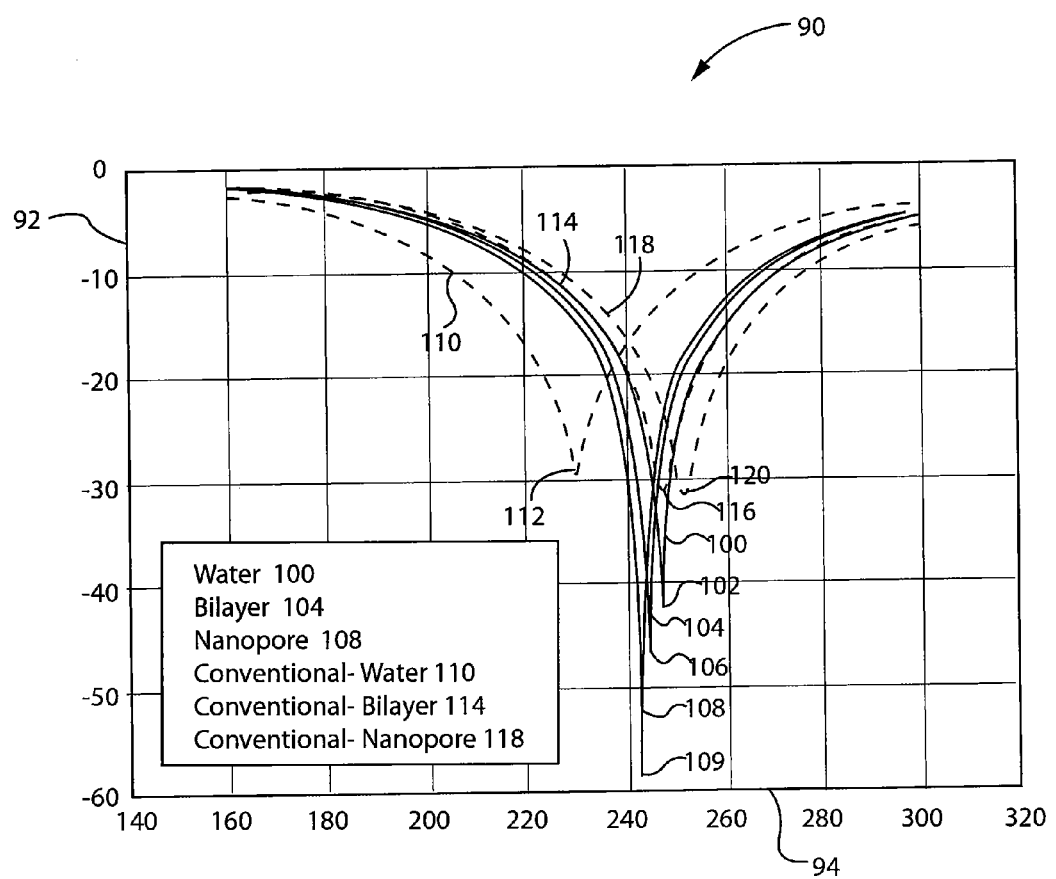
FIG. 5 is a graph illustrating calculated improvements for a device implemented in accordance with an embodiment of the invention.

Referring now to FIG. 5, a graph 90 illustrates comparative calculations for a device with an antenna implemented in accordance with an embodiment of the invention and a conventional case using a "tank circuit" that incorporates the impedance of the cell membrane via electrodes. A tank circuit of this type is described in U.S. Pat. No. 8,217,665 issued Jul. 10, 2012, assigned to the same assignee as the present invention and hereby incorporated by reference. Calculations are shown by way of total reflectance in decibels (dB) on the y-axis 92 as a function of radio frequency in Megahertz (MHz) on the x-axis 94. Three calculations are provided for the antenna case under various conditions in excess of 100 MHz, and another three calculations are provided for the conventional case under similar conditions.

With respect to the antenna case in accordance with an embodiment of the invention, the first calculation 100 provides a measurement for saline water. A peak reflection 102 of about −43 dB is calculated with a narrow center frequency band between 245 and 250 MHz. The second calculation 104 provides a measurement for a lipid bilayer surrounded by saline water. A peak reflection 106 of about −47 dB is calculated with a narrow center frequency band between 240 and 245 MHz. Finally, the third calculation 108 provides a measurement for a nanopore in the lipid bilayer. A peak reflection 109 of about −58 dB is calculated with a narrow center frequency between 240 and 245 MHz.

By way of relative comparison, with respect to the conventional case, the first calculation 110 again provides a measurement for saline water. A peak reflection 112 of about −29 dB is calculated with a wider center frequency between 220 and 240 MHz. The second calculation 114 again provides a measurement for a lipid bilayer surrounded by saline water. A peak reflection 116 of about −32 dB is calculated with a wider center frequency between 240 and 255 MHz. Finally, the third calculation 118 again provides a measurement for a nanopore in the lipid bilayer. A peak reflection 120 of about −33 dB is calculated with a wider center frequency between 240 and 255 MHz. Accordingly, measurements made with the antenna in accordance with an embodiment of the present invention provide improved sensitivity of at least an order of magnitude over past conventional systems thereby providing greater detection ability.

One or more specific embodiments of the present invention have been described above. It is specifically intended that the present invention not be limited to the embodiments and/or illustrations contained herein, but include modified forms of those embodiments including portions of the embodiments and combinations of elements of different embodiments as come within the scope of the following claims. For example, it will be appreciated that changes in the antenna shape and/or geometry may be made that are still within the scope and spirit of the invention.

It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the present invention unless explicitly indicated as being "critical" or "essential."

Certain terminology is used herein for purposes of reference only, and thus is not intended to be limiting. For example, terms such as "upper," "lower," "above," and "below" refer to directions in the drawings to which reference is made. Terms such as "front," "back," "rear," "bottom," "side," "left" and "right" describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first," "second" and other such numerical terms referring to structures do not imply a sequence or order unless clearly indicated by the context.

When introducing elements or features of the present disclosure and the exemplary embodiments, the articles "a," "an," "the" and "said" are intended to mean that there are one or more of such elements or features. The terms "comprising," "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

All of the publications described herein including patents and non-patent publications are hereby incorporated herein by reference in their entireties.

We claim:

1. A radio frequency analyzer for ion channels, the analyzer comprising:
   an electrically insulating support adapted to provide a support region for holding a membrane with ion channels;
   an antenna providing a first and second antenna lobe on opposite sides of the support region, the first and second antenna lobes having spaced apart apexes proximate to the support region, the lobes widening from the apexes with increased distance from the support region along an axis, the widening constrained substantially within bounding cones, one cone each sharing the apex of each lobe and having cone axes aligned with the axis;
   circuitry providing a radio frequency signal across the antenna lobes and determining changes of electrical flow across a cellular membrane positioned in the support region.

2. The radio frequency analyzer of claim 1, wherein the circuitry provides a radio frequency signal substantially near a resonant frequency of the antenna lobes and cellular membrane.

3. The radio frequency analyzer of claim 1, wherein the circuitry comprises a radio signal amplifier.

4. The radio frequency analyzer of claim 1, wherein the angle of each cone is between 25 and 40 degrees.

5. The radio frequency analyzer of claim 1, wherein the antenna lobes substantially form a bi-cone antenna.

6. The radio frequency analyzer of claim 1, wherein the first and second antenna lobes are comprised of a metallic micro-strip.

7. The radio frequency analyzer of claim 1, wherein after the first and second antenna lobes widen, the first and second antenna lobes straighten through an increased distance along the same axis.

8. The radio frequency analyzer of claim 7, wherein after the second antenna lobe straightens the second antenna lobe widens in opposite directions to either side then substantially forms around either side of the first antenna lobe.

9. The radio frequency analyzer of claim 1, wherein the radio frequency signal is in excess of 100 MHz.

10. A method of measuring ion channels comprising the steps of:
(a) placing a cellular membrane on an electrically insulating support adapted to provide a support region for holding a membrane with ion channels;
(b) applying a radio frequency signal across an antenna providing a first and second antenna lobe on opposite sides of the support region, the first and second antenna lobes having spaced apart apexes proximate to the support region, the lobes widening from the apexes with increased distance from the support region along an axis, the widening constrained substantially within bounding cones, one cone each sharing the apex of each lobe and having cone axes aligned with the axis;
(c) determining changes of impedance across the cellular membrane from measurement of a change in electrical resonance; and
(d) providing a measureable output indicating the determined change in impedance.

11. The method of claim 10, wherein the radio frequency signal is substantially near a resonant frequency of the antenna lobes and cellular membrane.

12. The method of claim 10, wherein a radio signal generator, a radio signal amplifier and a measurement circuit are used for determining changes of impedance.

13. The method of claim 10, wherein the cone angle is between 25 and 40 degrees.

14. The method of claim 10, wherein the antenna lobes substantially form a bi-cone antenna.

15. The method of claim 10, wherein the first and second antenna lobes are comprised of a metallic micro-strip.

16. The method of claim 10, wherein after the first and second antenna lobes widen, the first and second antenna lobes straighten through an increased distance along the same axis.

17. The method of claim 16, wherein after the second antenna lobe straightens the second antenna lobe widens in opposite directions to either side then substantially forms around either side of the first antenna lobe.

18. The method of claim 10, wherein the radio frequency signal is in excess of 100 MHz.

19. A radio frequency analyzer for ion channels, the analyzer comprising:
an electrically insulating support adapted to provide a support region for holding a membrane with ion channels;
an antenna providing a first and second antenna lobe on opposite sides of the support region, the first and second antenna lobes having spaced apart stubs proximate to the support region, the stubs traveling increased distance from the support region along an axis, wherein the stub of the second antenna lobe widens in opposite directions to either side and substantially forms around either side of the stub of the first antenna lobe;
circuitry providing a radio frequency signal across the antenna lobes and determining changes of electrical flow across a cellular membrane positioned in the support region.

20. The radio frequency analyzer of claim 19, wherein the circuitry comprises a radio signal amplifier.

\* \* \* \* \*